United States Patent [19]

Rüegg

[11] 4,439,629

[45] Mar. 27, 1984

[54] EXTRACTION PROCESS FOR BETA-CAROTENE

[75] Inventor: Rudolf Rüegg, Bottmingen, Switzerland

[73] Assignee: Hoffmann-La Roche Inc., Nutley, N.J.

[21] Appl. No.: 318,704

[22] Filed: Nov. 6, 1981

[51] Int. Cl.³ .............................................. C07C 7/10
[52] U.S. Cl. .................................. 585/803; 585/351; 585/837; 585/854; 585/867
[58] Field of Search ............... 585/803, 837, 351, 853, 585/854, 867

[56] References Cited

U.S. PATENT DOCUMENTS

| | | | |
|---|---|---|---|
| 1,786,095 | 12/1930 | Takahashi | 47/1.4 |
| 2,394,278 | 2/1946 | Wall et al. | 585/803 |
| 2,446,116 | 7/1948 | Wall et al. | |
| 3,238,252 | 7/1977 | Maggi | 47/1.4 |
| 4,115,949 | 9/1978 | Avron et al. | 47/1.4 |
| 4,199,895 | 4/1980 | Avron et al. | 47/1.4 |

OTHER PUBLICATIONS

Chemical Abstract 83: 129939f (Geleskul et al.).
Chemical Abstract 88: 20531u (Ruene).
Chemical Abstract 95: 95438n (Ben–Amotz et al.).

*Primary Examiner*—Delbert E. Gantz
*Assistant Examiner*—A. Pal
*Attorney, Agent, or Firm*—Jon S. Saxe; George M. Gould; William H. Epstein

[57] ABSTRACT

A process for extracting either or both beta-carotene or glycerine from algae containing these substances, especially from algae of the genera Dunaliella.

6 Claims, No Drawings

EXTRACTION PROCESS FOR BETA-CAROTENE

BACKGROUND OF INVENTION

It has been known for a long time that certain kinds of algae, especially algae found in strong salt-containing waters, such as, for example, algae of the genera Dunaliella, contain, inter alia, considerable amounts of beta-carotene and glycerine. However, the isolation of these substances from the algae material has hitherto presented considerable difficulties, since the latter must either firstly be separated from the salt water in which it has been growing, or in the extraction of the mixture of salt water and algae, very large amounts of organic extraction agents must be used. Moreover, the extraction yielded not only beta-carotene, but also chlorophyll contained in the algae, which made the isolation of pure beta-carotene very difficult. In addition, the mixture required more or less vigorous shaking during the extraction with the organic solvent in order to rupture the algae cells.

There accordingly exists a need for a process which will enable not only beta-carotene but also glycerine to be extracted from algae in a simple manner, with satisfactory yields and with the greatest possible purity.

SUMMARY OF INVENTION

In accordance with this invention, either or both of beta-carotene or glycerine can be extracted from algae. If it is desired to extract beta-carotene, the algae are first treated with calcium hydroxide and then filtered. The residue from this filtration is treated with a beta-carotene solvent which removes the beta-carotene from the residue and into the solvent. The beta-carotene can be recovered from the solvent by conventional means. If it is desired to extract glycine, the filtrate from the treatment of the algae with calcium hydroxide is neutralized, concentrated and the residue from the solid is treated with a lower alkanol to remove glycerine from the residue.

DETAILED DESCRIPTION

In accordance with this invention, any algae material which contains either or both beta-carotene or glycerine, or preferably contains both of these materials can be utilized as the starting material in this process. This algae material used as the starting material can be used in impure form in the process in accordance with the invention, i.e. the algae used need not be separated completely from salt water present before the treatment with the calcium hydroxide.

The treatment of the algae material with calcium hydroxide is preferably carried out under an inert gas atmosphere (e.g. under nitrogen, argon) and at a temperature of about 50° C. to about 100° C., with the reflux temperature of the mixture being especially preferred. The heating is preferably carried out for about 2 to 6 hours. However, if desired, also longer heating times can be used. By means of this treatment, the chlorophyll present in the algae is converted into calcium salts which are insoluble in the solvents for beta-carotene mentioned hereinafter.

The filter residue can be subjected to the extraction in the moist condition, for example, water-moist or washed with methanol or ethanol. However, it is preferably completely dried before the extraction, for example, in a vacuum drying oven. The extraction is carried out in a manner known per se with a solvent for beta-carotene such as, for example, a halogenated hydrocarbon (e.g. methylene chloride) or with a solvent which is not soluble in water (e.g. an aliphatic or aromatic hydrocarbon such as hexane, benzene, toluene or also petroleum ether and the like). In fact, any conventional organic solvent for beta-carotene can be used in carrying out this process. The solvent removes beta-carotene from the residue and into the solvent. After extraction of the residue with the solvent, beta-carotene can be recovered from the solvent by any conventional means. Among the conventional means that can be used to recover beta-carotene from the solvent are included evaporation, distillation, etc.

In order to isolate the glycerine from the filtrate, the filtrate is conveniently firstly neutralized to a pH of from about 6 to 8 with acid. Any conventional inorganic acid can be utilized. Generally, it is preferred to utilize an aqueous inorganic acid such as aqueous hydrochloric or aqueous sulfuric acid, etc. The resulting solution is then concentrated and the residue is purified by treatment with a lower alcohol containing from 1 to 5 carbon atoms, preferably with isopropanol.

In carrying out the concentration of the neutralized filtrate, any conventional method can be utilized. The residue which results from the concentration of the neutralized filtrate solution is treated with a lower alkanol by simple addition of the lower alkanol to the residue. The lower alkanol removes the glycerine from the residue. Glycerine can be recovered from the lower alkanol solution by conventional means such as evaporation.

The following Example illustrates the present invention:

EXAMPLE 500 g of wet algae slurry are heated at about 100° C. for 2 hours with 75 g of calcium hydroxide while stirring and gassing with argon. After cooling to about 50° C., the mixture is suction filtered, if desired with the addition of a small amount of water, and back-washed with water. A pale yellow-green colored, clear filtrate is obtained. The filter residue is then completely dried and extracted with methylene chloride in a Soxhlett apparatus until the extract is almost colorless. About 110 g of a green colored insoluble powder remain behind. The methylene chloride is now distilled off and the semi-solid red residue is treated with 200 ml of hexane (if necessary while warming and swirling so that all material loosens from the flask wall) and left to stand at room temperature overnight. The mixture is filtered and there are obtained 1.9 g of crude carotene (about 90%). This crude carotene is recrystallized from methylene chloride/methanol to give 1.3 g of all-trans-beta-carotene (94.5% pure): UV$\lambda_{max}$=450 nm, $E_1^1$=2560 (in hexane).

The aforementioned pale yellow-green colored filtrate is neutralized to pH 6–7 with about 50% by weight aqueous sulfuric acid. The oslution obtained is, if desired after filtering off the precipitated calcium sulfate, evaporated under a water-jet vacuum. About 120 g of a yellowish colored viscose resin are obtained. This is shaken for several hours with 300 ml of isopropanol, undissolved salt is filtered off and the filtrate is evaporated. This procedure is repeated once more with 200 ml of isopropanol. There are obtained 23 g of pale yellow colored crude glycerine which is distilled in a high vacuum. 18.5 g of pure glycerine are thus obtained at 0.03 mm Hg and 95° C., $n_D^{20} = 1.4740$.

I claim:

1. A process for extracting beta-carotene from algae containing beta-carotene comprising treating the algae with calcium hydroxide at a temperature of 50° C. to 100° C. to saponify the chlorophyll present in the algae and produce a residue, treating said residue with a solvent for beta-carotene which removes the beta-carotene from said residue, and thereafter recovering beta-carotene from said solvent.

2. The process of claim 1 wherein said algae is of the genera Dunaliella.

3. The process of claim 1 wherein the treatment of the algae material with the calcium hydroxide is carried out for about 2–6 hours.

4. The process of claim 1 wherein the treatment of the crude algae material with the calcium hydroxide is carried out under an inert gas atmosphere.

5. The process of claim 1 wherein the filter residue is dried before treating with a solvent.

6. The process of claim 1 wherein the solvent is methylene chloride, hexane or high-boiling petroleum ether.

* * * * *

UNITED STATES PATENT AND TRADEMARK OFFICE
CERTIFICATE OF CORRECTION

PATENT NO. : 4,439,629
DATED : March 27, 1984
INVENTOR(S) : Rudolf Ruegg

It is certified that error appears in the above—identified patent and that said Letters Patent is hereby corrected as shown below:

On the title page the following should be inserted:
-- [30] Foreign Application Priority Data
    Nov. 20, 1980      [CH]    Switzerland.....8594/80--.

Signed and Sealed this

Eighteenth Day of September 1984

[SEAL]

Attest:

GERALD J. MOSSINGHOFF

Attesting Officer

Commissioner of Patents and Trademarks